United States Patent [19]

Fisher

[11] Patent Number: 5,200,149

[45] Date of Patent: * Apr. 6, 1993

[54] CHEMICAL TEST KIT FOR USE IN DETECTING IMPURITIES IN OIL SAMPLES

[75] Inventor: David J. Fisher, North Adams, Mass.

[73] Assignee: Electric Power Research Institute, Inc., Palo Alto, Calif.

[*] Notice: The portion of the term of this patent subsequent to Aug. 11, 2004 has been disclaimed.

[21] Appl. No.: 554,782

[22] Filed: Jul. 18, 1990

Related U.S. Application Data

[60] Continuation of Ser. No. 370,231, Jun. 22, 1989, Pat. No. 4,957,871, which is a division of Ser. No. 50,924, May 15, 1987, Pat. No. 4,873,056, which is a continuation of Ser. No. 529,154, Sep. 2, 1983, Pat. No. 4,686,192.

[51] Int. Cl.$^5$ .................... G01N 21/78; G01N 31/16
[52] U.S. Cl. ........................ 422/61; 422/58; 422/75; 436/60; 436/165; 436/163
[58] Field of Search ................ 436/165, 166, , 60, 436/126, 163; 422/61, 58, 60, 75; 435/296, 300

[56] References Cited

U.S. PATENT DOCUMENTS

| | | |
|---|---|---|
| 3,022,141 | 2/1962 | Grosskopf .................. 422/60 |
| 3,068,855 | 12/1962 | Furlong ..................... 422/58 |
| 3,715,189 | 2/1973 | Nighohossian et al. ...... 422/61 |
| 4,300,910 | 11/1982 | Pannwitz .................... 422/60 |
| 4,686,192 | 8/1987 | Fisher ........................ 422/61 |
| 4,873,056 | 10/1989 | Fisher ........................ 422/61 |
| 4,957,871 | 9/1990 | Fisher ........................ 436/165 |
| 5,013,667 | 5/1991 | Lynn et al. ................. 436/60 X |
| 5,028,543 | 7/1991 | Finch et al. ................ 436/60 X |

FOREIGN PATENT DOCUMENTS 1539695 1/1979 United Kingdom .
1586569 3/1981 United Kingdom .

Primary Examiner—Robert J. Hill, Jr.
Attorney, Agent, or Firm—Heller, Ehrman, White & McAuliffe

[57] ABSTRACT

A chemical test kit and method for detecting the presence of impurities in an oil sample is provided. The test kit is comprised of two flexible translucent or transparent containers, each with at least one breakable capsule mounted within it. One of the flexible containers has a means for separating an aqueous layer from an oil layer. The capsules contain reagents capable of extracting the impurity to be detected from the oil into an aqueous layer and indicating the presence of a threshold concentration of the impurity. The method involves the steps of introducing an oil sample into a first flexible container, breaking the capsule within it by squeezing the flexible container in the vicinity of the capsule, transferring the aqueous layer to the second container, and breaking the capsule within the second container in the same manner. A chemical reaction occurs in the second container indicating whether the impurity is present at a given threshold concentration.

20 Claims, 1 Drawing Sheet

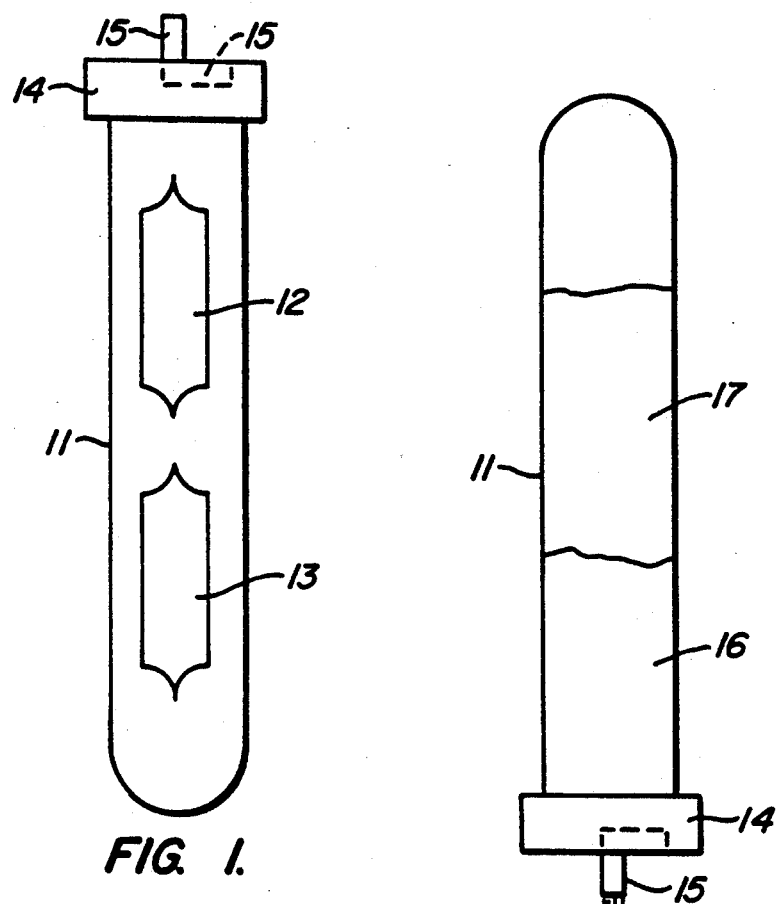
FIG. 1.
FIG. 3.
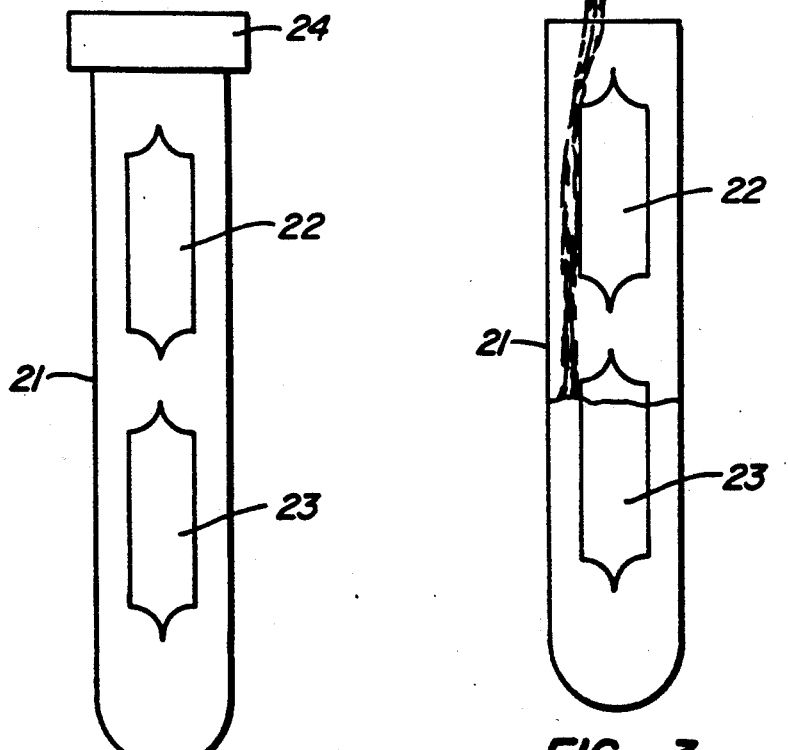
FIG. 2.

CHEMICAL TEST KIT FOR USE IN DETECTING IMPURITIES IN OIL SAMPLES

This is a continuation of application Ser. No. 370,231, filed Jun. 22, 1989, now U.S. Pat. No. 4,957,871, which in turn is a division of application Ser. No. 050,924, filed May 15, 1987, now U.S. Pat. No. 4,873,056, which in turn, is a continuation of application Ser. No. 529,154, filed Sept. 2, 1983, now U.S. Pat. No. 4,686,192.

The present invention is directed to a chemical test kit and method to be used in the field for determining the presence of threshold amounts of impurities in an oil sample. Specifically, the present invention is directed to a chemical test kit and method to be used in the field for determining the presence of threshold amounts of polychlorinated biphenyl in transformer oil.

BACKGROUND OF THE INVENTION

A method and testing container for detecting the presence of certain components or substances in biological fluids is disclosed in U.S. Pat. No. 3,036,894. The testing container has a flexible tubular body with non-communicating individual compartments, some of which contain reagents, which allow for transfer of the contents of the preceding compartment to a succeeding compartment. The substance to be tested is passed sequentially through each compartment and intermixed with the substances contained therein until it reaches the final compartment where the tested substance can be removed for test reading and conclusion.

A small testing tube for the chemical analysis of gas compositions is disclosed in U.S. Pat. No. 3,022,141. The testing tube disclosed therein contains three or more separately arranged reagents or layers of reagents, one or more reagents are placed in one or more breakable ampoules. The testing tubes are breakable in the area of the ampoules but are provided with a flexible reinforcing coating. The gas flows through the testing tube contacting each reagent in sequence and finally reaches the indicator layer where the presence of the particular component is detected. Both ends of the testing tube are sealed and are broken just prior to testing.

Another method for measuring gas, vapor and aerosol components in an air sample using a glass testing tube is disclosed in U.S. Pat. No. 4,300,910. The disclosed testing tube has a breakable tip at each end and contains a breakable ampoule, an entraining filter, a reaction layer, an empty tube chamber and a liquid lock in that order. As the gas passes through the testing tube, the particles are entrained by the filter. The ampoule is broken to direct a solvent through the filter to dissolve the materials and to pass them into a reaction layer where a color reaction takes place. The color reaction is visible in the empty chamber and indicates which components are present in the air sample.

There is a need for a simple chemical test method and kit which can be used in the field by a relatively untrained person to determine whether the oil in a transformer has been contaminated with polychlorinated biphenyl [hereinafter sometimes referred to as PCB] in excess of the Environmental Protection Agency regulations. There are currently an estimated 20,000,000 transformers which will have to be analyzed for polychlorinated biphenyl contamination in order to comply with the current regulations. Many of these units are PCB-free, that is, they contain less than 50 ppm of PCB's. The method and chemical test kit of the present invention could eliminate the necessity of costly laboratory analysis on about 60% of these transformers.

SUMMARY OF THE INVENTION

In general, it is an object of the present invention to provide a novel, simple, reliable, and routine chemical test kit and method for use in the field to determine the presence of impurities in an oil sample.

Specifically, it is an object of the invention to provide a novel, simple, reliable, and routine chemical test method and kit for use in the field to determine whether the polychlorinated biphenyl content in transformer oil is close enough to the Environmental Protection Agency regulation limit to require more accurate laboratory analysis.

Another object is to provide a chemical test method which can be performed by someone with no chemical training.

Another object of the invention is to provide a chemical test kit and method which will in some cases eliminate the necessity of costly laboratory analysis.

Another object is to provide an inexpensive disposable chemical test kit.

In general, the present invention provides a chemical test kit and a method for detecting the presence of certain impurities in an oil sample. The chemical test kit comprises two flexible containers, each with at least one breakable capsule mounted within it. The first container has a capsule containing a reagent capable of reacting with the impurity to be detected and extracting the impurity from the oil into an aqueous layer. The first container also has a means for separating the aqueous layer from the oil layer, preferably a cap with a nozzle which can be opened to pour the aqueous layer from the container. The second container has a capsule containing a reagent which is capable of visibly reacting with the impurity to be detected, indicating the presence of that impurity at a certain threshold concentration.

The particular reagent contained in each capsule, and the precise amount and concentration of each reagent, will be determined based upon which impurity is to be detected in the oil sample, and premeasured quantities of each reagent will be pre-packaged in the capsules of the chemical test kit.

The method involves the steps of introducing an oil sample into a first flexible container, breaking a capsule in the first container, shaking the container, and after the aqueous layer has formed, separating the aqueous layer from the oil layer by transferring the aqueous layer into a second flexible container, breaking a capsule in the second container, and shaking the container, the color of the solution will indicate the presence of the impurity at a threshold concentration.

Various types of analysis may be performed with the chemical test kit and method of the present invention, for instance, the kit can be equipped to determine the presence of impurities in oil samples, such as pesticides and/or degreasing materials, inhibitors, dissolved gases, acids, and polychlorinated biphenyl.

Additional objects and features of the invention will appear from the following description in which the preferred embodiments have been set forth in detail in conjunction with the accompanying drawings.

BRIEF DESCRIPTION OF THE DRAWINGS

FIG. 1 is a side elevational view schematically illustrating the first container of a preferred embodiment of the chemical test kit of the present invention.

FIG. 2 is a side elevational view schematically illustrating the second container of a preferred embodiment of the chemical test kit of the present invention.

FIG. 3 is a side elevational view schematically illustrating a preferred embodiment of the chemical test kit in operation.

DETAILED DESCRIPTION OF THE INVENTION

Referring to FIGS. 1 and 2, a preferred embodiment of the chemical test kit of the present invention is illustrated. The chemical test kit is comprised of two flexible transparent or translucent containers. FIG. 1 represents a first flexible transparent container in which the impurity to be detected is extracted from the oil into an aqueous layer. FIG. 2 represents a second flexible transparent container in which a chemical reaction takes place, indicating by the color of the solution, the presence of the impurity to be detected at a threshold concentration.

Referring to FIG. 1, the container 11 is comprised of a flexible transparent material, preferably polypropylene or polyethylene. The container has at least one breakable capsule 12 mounted within it and containing a chemical reagent. In certain applications, two chemical reagents may be necessary to perform the desired reaction and thus two breakable capsules 12 and 13 would be mounted within the container 11 as shown in FIG. 1. The container in FIG. 1 also has a cap 14 with a nozzle 15 shown in the open position by solid lines and in the closed position by broken lines.

Referring to FIG. 2, the second container of the chemical test kit, container 21, is also comprised of a flexible transparent material, preferably polypropylene or polyethylene. There is at least one breakable capsule 22 mounted within container 21 containing a reagent which will indicate the presence of the impurity to be detected. In certain applications, two reagents may be necessary to perform the desired chemical reaction, thus two breakable capsules 22 and 23 will be mounted within the container 21. A cap 24 is also provided.

The method of detecting the presence of certain substances in an oil sample using the chemical test kit of the present invention involves removing cap 14 from container 11, introducing an oil sample into container 11, and replacing cap 14 with nozzle 15 in the closed position. If there is more than one encapsulated reagent, the capsules are broken in sequence depending upon which reagent must react first with the impurity to be detected. Assuming that two reagents are required in the particular application, the operator will break the first capsule 12, preferably by squeezing the flexible container in the vicinity of the capsule, shake container 11, break the second capsule 13 in the same manner, shake container 11 and allow the chemical reactions to take place. One of the reagents encapsulated should be in an aqueous solution or at some point an aqueous solution should be introduced into container 11 to allow the substance to be extracted from the oil into an aqueous layer.

For those applications where the oil chemically interferes with the desired reaction, after the two layers have been formed the container 11 should be inverted so that the aqueous layer 16 forms in the end near the cap 14 as shown in FIG. 3. Cap 24 is then removed from the second container 21. The nozzle 15 on cap 14 of container 11 is then opened and the aqueous layer 16 in container 11 flows into the second container 21. The nozzle should be closed before the oil layer begins to enter the second container. At this point, cap 24 can be replaced and the operator can break the first capsule 22, preferably by squeezing the flexible container in the vicinity of the capsule, shake the container, break the second capsule 23 in the same manner, if a second capsule is present, and shake the container. At this point a chemical reaction will take place visibly indicating to the operator whether the substance to be detected is present at the threshold concentration.

In some applications, the oil may not chemically interfere with the indicating reaction and it will not be necessary to separate the aqueous layer from the oil layer prior to initiating the indicating reaction. In such cases, all necessary reagents can be encapsulated in one flexible translucent or transparent container, and the test to determine the prescence of the impurities can be conducted in a single container.

The particular reagent, the number of encapsulated reagents, and the amount and concentration of each reagent will vary depending upon which substance is being detected.

When the chemical test kit of the present invention is to be used for determining the presence of polychlorinated biphenyl in transformer oil, the capsules in the kit will contain reagents necessary to strip the chlorine from the polychlorinated biphenyl molecule and to detect the presence of a threshold concentration of the chloride ion thus formed.

A number of techniques using metallic sodium or lithium and suitable solvents for stripping the chlorine from the polychlorinated biphenyl molecule are known. The chlorine is converted to sodium or lithium chloride. The amount of chloride formed is an indirect measure of the PCB originally present. In the presence of water, sodium or lithium chloride produces chloride ions which are easily measurable in minute concentrations using a dye indicator with a mercury titrant.

Referring to FIG. 1, when the kit is to be used to detect the presence of polychlorinated biphenyl, the first container 11 will contain at least one breakable capsule 12 containing an alkali metal, such as sodium or lithium. When an oil sample is introduced into container 11 and capsule 12 is broken releasing the alkali metal, a chemical reaction begins in which the chlorine atoms on the polychlorinated biphenyl molecule are stripped from the carbon in the biphenyl molecule. The chlorine is replaced by hydrogen atoms removed from other molecules or the biphenyl residue couples with other biphenyl molecules. When all the chlorines, have been replaced by hydrogens, the polychlorinated biphenyl is converted to biphenyl. The chlorine molecules form an alkali chloride, such as sodium chloride or lithium chloride. The reaction occurs with finely-dispersed alkali metal, but the rate of the process can be increased greatly if the reactive alkali metal is distributed on a molecular basis. Thus, the preferable reagent for capsule 12 is an organo-alkali salt, such as organo-sodium salt or organo-lithium salt.

Metallic sodium is a preferred alkali metal reagent for the present invention. Metallic sodium reacts with small aromatic hydrocarbon molecules, such as those containing up to twenty carbon atoms, to form organo-sodium salts. These salts can then dissolve in oil and react with the polychlorinated biphenyl to form biphenyl and sodium chloride. The aromatic hydrocarbon reverts to its original form. In order to build up quantities which will give attractive PCB conversion rates, the organo-metallic salt must be stabilized by the presence of additional molecules, known as ligands. The ligands serve to solvate the sodium salt and increase its stability. A preferred aromatic hydrocarbon to form a sodium salt is naphthalene and a preferred stabilizing ligand can be selected from the group consisting of tetrahydrofuran and diethylene glycol dimethyl ether. The preferred stabilizing ligand according to the present invention is diethylene glycol dimethyl ether.

If lithium is used as the alkali metal to strip chlorine from polychlorinated biphenyl, a lithium salt can be formed by reacting metallic lithium with the butane molecule yielding butyl lithium. Butyl lithium would yield lithium chloride on reaction with polychlorinated biphenyl.

After the chlorine has been stripped from the polychlorinated biphenyl in the oil sample in container 11, an aqueous solution should be added to extract the chloride ions into an aqueous phase. An aqueous solution can be added to container 11 by removing cap 14 or a second capsule containing an aqueous solution can be mounted within container 11 and broken after the conversion of polychlorinated biphenyl to chloride to extract the chloride into an aqueous layer.

A preferred embodiment of the present invention has two capsules mounted within container 11. The first capsule 12 contains the metallic sodium dispersed in a light oil and the second capsule 13 contains naphthalene, an organo-metallic salt former, and diethylene glycol dimethyl ether, a stabilizing ligand. An acid/buffer solution, such as an aqueous solution containing nitric acid and disodium phosphate, is added to container 11 after the necessary reactions have taken place to dechlorinate the polychlorinated biphenyl in order to extract the chloride ions into an aqueous layer. The acid/buffer solution is contained in container 21 and is not encapsulated in a breakable capsule.

When the chemical test kit is being used to detect the presence of PCB in transformer oil, container 21 has at least two breakable capsules 22 and 23 mounted within it. One capsule contains a mercury titrant and the other capsule contains a dye indicator. The amount of mercury titrant should correspond to that required to react with all of the chloride ions in a threshold concentration of PCB. The current Environmental Protection Agency regulation considers oil to be PCB-free if it contains less than 50 ppm of PCB. Therefore, the amounts and concentrations of the various reagents used in the kit will be chosen to differentiate between chlorides corresponding to less than or greater than 50 ppm of PCB. When the threshold concentration of PCB is 50 ppm, a preferred mercury titrant is mercuric nitrate and a preferred dye indicator is diphenyl carbazone or a mixture of diphenyl carbazone and bromphenyl blue. The most preferred indicator for the present invention is diphenyl carbazone alone.

When the aqueous layer containing the chloride ions is added to container 21 and the capsules 22 and 23 containing the mercuric titrant and the dye indicator are broken, the solution should assume one of two colors which indicate whether the PCB content is more or less than a threshold concentration. When the dye indicator is diphenyl carbazone or diphenyl carbazone and bromphenyl blue, the chloride ions react with the mercuric ions in the titrant to form mercuric chloride while excess mercuric ions and the diphenyl carbazone dye indicator react to form a blue-violet color indicating a PCB content of less than 50 ppm. If the amount of chloride ions present is equivalent to a polychlorinated biphenyl content of greater than 50 ppm, there are no mercuric ions left to react with the dye indicator, resulting in a colorless to yellow solution.

The method for detecting the presence of polychlorinated biphenyl in an oil sample, utilizing the chemical test kit described above, involves the steps of: introducing an oil sample into the first container 11, replacing the cap 14, breaking capsule 12, preferably by squeezing the flexible container in the vicinity of capsule 12, thereby releasing the alkali metal, shaking the container 11 thereby initiating the chemical reaction whereby the alkali metal strips the chlorine from polychlorinated biphenyl to form an alkali chloride, adding a buffer/acid solution to container 11, shaking container 11 thereby extracting the alkali chloride into an aqueous layer, separating the aqueous layer from the oil layer by transferring the aqueous layer through a separating means 15 on container 11 into the second container 21, breaking the first capsule 22 containing a mercury titrant in the second container 21, preferably by squeezing the flexible container in the vicinity of capsule 22, thereby releasing the mercury titrant, shaking container 21, breaking the second capsule 23 containing a dye indicator in the same manner, shaking container 21, and observing the color of the solution to determine whether the threshold concentration of polychlorinated biphenyl is present in the oil sample.

The preferred method when the PCB content of 50 ppm is to be detected involves breaking two capsules in container 11, the first containing an organo-metallic salt former and a stabilizing ligand, preferably naphthalene and diethylene glycol dimethyl ether, and the second containing sodium dispersed in a light oil. Preferably, the acid/buffer solution is contained in container 21 and is poured into container 11 after both capsules 12 and 13 have been broken and the chemical reaction has taken place. This results in the extraction of the chloride ions into the aqueous layer and allows for subsequent separation of the aqueous layer from the oil layer by transferring the aqueous layer into container 21. Preferably, the separation step involves inverting container 11 with nozzle 15 in the closed position to allow the aqueous layer to form adjacent to the cap and positioning container 21 under container 11 so that when the nozzle 15 is opened the aqueous layer in container 11 is poured into container 21. The nozzle is closed when the aqueous layer is in container 21 so that the oil layer is retained in container 11. With the aqueous layer in container 21, the two capsules 22 and 23 are broken and the indicating reaction can take place. Preferably, the first capsule contains mercuric nitrate and the second capsule contains biphenyl carbazone.

When the chemical test kit is used to determine the presence of more than 50 ppm of PCB's in transformer oil, the preferred reagents, concentrations and number of capsules in each container are as follows. The first flexible container contains two capsules, one capsule contains 200 $\mu$l of a 20% sodium dispersion in light oil, the second capsule contains 200 $\mu$l of a 4:1 ratio of diethylene glycol dimethyl ether and naphthalene; the second flexible container contains 7 ml. of a buffer/acid solution and two capsules, one capsule containing 1 ml. of 0.0012 Molar mercuric nitrate, the second capsule containing 0.25 ml. of 0.1% diphenyl carbazone. In order to achieve the desired end color for an oil sample containing more than 50 ppm of PCB's and/or less than 50 ppm of PCB's, a 5 ml. oil sample should be tested.

EXAMPLE 1

Twelve mg. of sodium was placed in an empty 12 ml. polypropylene test tube. Two hundred µl of diethylene glycol dimethyl ether and 50 mg. of naphthalene were added to a 3 ml. sample of oil externally. Five ml. of oil were then added to the test tube and the test tube was shaken. Five ml. of water containing nitric acid, disodium phosphate buffer, and diphenyl carbazone indicator were added to the tube and the tube was again shaken. Mercuric nitrate equivalent to 21 ppm of chloride was then added. The samples which originally contained 40 ppm of PCB's produced a violet-blue color in the aqueous phase. The samples which contained 50 ppm or more of PCB's resulted in no color change, a yellow color persisted.

What is claimed is:

1. A kit for detecting the presence of certain substances in oil, comprising:
    (a) a first flexible container, having at least one breakable capsule mounted within said first container and containing a reagent selected to react with a specific impurity contained in a sample of oil that is placed into said first container to produce a product that can be extracted from the oil into an aqueous layer and means for separating the aqueous layer from an oil layer; and
    (b) a second flexible container, having at least one breakable capsule mounted within said second container and containing a chemical reagent selected to react with said product in said aqueous layer thereby indicating the presence of a threshold concentration of the impurity to be detected.

2. A kit for detecting the presence of polychlorinated biphenyl in an oil sample comprising:
    a) a first flexible container having at least one breakable capsule mounted within said first container containing an alkali metal and means for separating an aqueous layer from an oil layer; and
    b) a second flexible container, having at least two breakable capsules mounted within said second container, one of said capsules containing a mercury titrant and the other said capsule containing a dye indicator.

3. A kit according to claim 2 wherein said alkali metal is selected from the group consisting of sodium and lithium.

4. A kit according to claim 2 wherein said alkali metal is sodium.

5. A kit according to claim 2 wherein said mercury titrant is mercuric nitrate.

6. A kit according to claim 2 wherein said dye indicator comprises diphenyl carbazone and bromphenyl blue.

7. A kit according to claim 2 wherein said dye indicator is diphenyl carbazone.

8. A kit according to claim 2 wherein said first container also has a breakable capsule containing a stabilizing ligand and an organo-metallic salt former, mounted within said container.

9. A kit according to claim 8 wherein said organo-metallic salt former comprises an aromatic hydrocarbon containing up to twenty carbons.

10. A kit according to claim 9 wherein said aromatic hydrocarbon is naphthalene.

11. A kit according to claim 8 wherein said stabilizing ligand is selected from the group consisting of tetrahydrofuran and diethylene glycol dimethyl ether.

12. A kit according to claim 8 wherein said ligand is diethylene glycol dimethyl ether.

13. A kit according to claim 2 wherein said second container contains an acid/buffer solution.

14. A kit according to claim 13 wherein said acid/buffer solution is an aqueous solution containing nitric acid and disodium phosphate.

15. A kit according to claim 2 wherein said first container is mounted with two breakable capsules, one of said capsules in said first container contains about 200 µl of a 20% sodium dispersion in a light oil, wherein said other capsule in said first container contains abut 200 µl of a 4:1 ratio of diethylene glycol dimethyl ether and naphthalene, wherein said second container contains about 7 milliliters of a buffer/acid solution, wherein one of said capsules in said second container contains about 1 milliliter of 0.0012 Molar mercuric nitrate, wherein said other capsule in said second container contains about 0.25 milliliters of 0.1% diphenyl carbazone.

16. A kit according to claim 2 wherein said first and second flexible containers are comprised of polyethylene.

17. A kit according to claim 2 wherein said first and second flexible containers are comprised of polypropylene.

18. A kit according to claim 2 wherein said first and second flexible containers are comprised of a translucent material.

19. A kit according to claim 2 wherein said first and second flexible containers are comprised of a transparent material.

20. A kit according to claim 2 wherein said separating means comprises a cap with a nozzle adapted to be closed during a chemical reaction and opened for separating an aqueous layer from an oil layer.

* * * * *